United States Patent
Gosselin et al.

(10) Patent No.: US 10,781,219 B2
(45) Date of Patent: Sep. 22, 2020

(54) PROCESS FOR THE PREPARATION OF (S)-2-((2-((S)-4-(DIFLUOROMETHYL)-2-OXOOXAZOLIDIN-3-YL)-5,6-DIHYDROBENZO[F]IMIDAZO[1,2-D][1,4]OXAZEPIN-9-YL)AMINO) PROPANAMIDE

(71) Applicant: Genentech, Inc., South San Francisco, CA (US)

(72) Inventors: Francis Gosselin, South San Francisco, CA (US); Chong Han, South San Francisco, CA (US); Theresa Cravillion, South San Francisco, CA (US); Sean M. Kelly, South San Francisco, CA (US); Scott Savage, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/441,765

(22) Filed: Jun. 14, 2019

(65) Prior Publication Data

US 2019/0292201 A1 Sep. 26, 2019

Related U.S. Application Data

(63) Continuation of application No. PCT/EP2017/083143, filed on Dec. 15, 2017.

(60) Provisional application No. 62/434,836, filed on Dec. 15, 2016.

(51) Int. Cl.
*C07D 498/04* (2006.01)

(52) U.S. Cl.
CPC .................. *C07D 498/04* (2013.01)

(58) Field of Classification Search
CPC ..................................................... C07D 498/04
See application file for complete search history.

(56) References Cited

U.S. PATENT DOCUMENTS

| | | | |
|---|---|---|---|
| 8,242,104 B2 | 8/2012 | Blaquiere et al. | |
| 8,343,955 B2 | 1/2013 | Blaquiere et al. | |
| 9,303,043 B2 | 4/2016 | Angelaud et al. | |
| 9,650,393 B2 | 5/2017 | Braun et al. | |
| 9,670,228 B2 | 6/2017 | Blaquiere et al. | |
| 10,112,932 B2 | 10/2018 | Braun et al. | |
| 2018/0339997 A1 | 11/2018 | Chakravarty et al. | |

FOREIGN PATENT DOCUMENTS

| | | |
|---|---|---|
| WO | 2011/036280 A1 | 3/2011 |
| WO | 2014/140073 A1 | 9/2014 |
| WO | 2017/001645 A1 | 1/2017 |

OTHER PUBLICATIONS

Edgar et al., "Prelinical characterization of GDC-0077, a specific PI3K alpha inhibitor in early clinical development" Cancer Res. (Proceedings: AACR Annual Meeting 2017; Apr. 1-5, 2017, Washington, D.C.), 77(13 Suppl Suppl. Abstract 156):1 (2017).
"International Preliminary Report on Patentability—PCT/EP2017/083143": pp. 1-7 (Jun. 27, 2019).
"International Search Report—PCT/EP2017/083143 dated Mar. 20, 2018":1-5 (Mar. 20, 2018).
Ndubaku et al., "Discovery of 2-{3-[2-(1-Isopropyl-3-methyl-1H-1,2-4-triazol-5-yl)-5,6-dihydrobenzo[f]imidazol[1,2-d][1,4]oxazepin-9-yl]-1H-pyrazol-1-yl}-2-methylpropanamide (GDC-0032): A β-Sparing Phosphoinositide 3-Kinase Inhibitor with High Unbound Exposure and Robust in Vivo Antitumor Activity" J. Med. Chem. 56(11):4597-4610 ( 2013).
Olivero et al., "Discovery of GDC-0032: A beta-sparing PI3K inhibitor active against PIK3CA mutant tumors." Cancer Res. (Abstract DDT02-01), 73(8 Suppl Suppl.):3 ( 2013).
Staben et al., "Discovery of GDC-007, a highly isoform selective inhibitor of PI3Ka that promotes selective loss of mutant-p110a" Cancer Res. (Abstract DDT02-01), 77(Suppl 13) (Jul. 2017).

*Primary Examiner* — Brenda L Coleman
(74) *Attorney, Agent, or Firm* — Zong-Qiang Bill Tian

(57) ABSTRACT

Methods of making benzoxazepin oxazolidinone compounds as well as synthetic intermediates are described, including compound 18, having the structure:

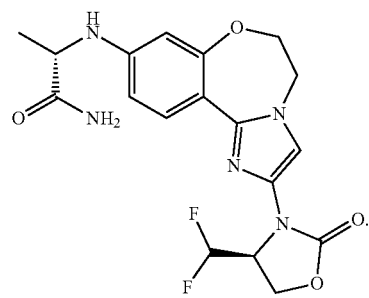

20 Claims, No Drawings

PROCESS FOR THE PREPARATION OF (S)-2-((2-((S)-4-(DIFLUOROMETHYL)-2-OXOOXAZOLIDIN-3-YL)-5,6-DIHYDROBENZO[F]IMIDAZO[1,2-D][1,4]OXAZEPIN-9-YL)AMINO) PROPANAMIDE

CROSS-REFERENCE TO RELATED APPLICATIONS

This application is a continuation of International Application No. PCT/EP2017/083143 filed 15 Dec. 2017, which claims the benefit of priority to U.S. Provisional Patent Application No. 62/434,836 filed 15 Dec. 2016, the contents of which are hereby incorporated by reference in their entirety.

FIELD OF THE INVENTION

The invention relates to methods of making benzoxazepin oxazolidinone compounds, and useful intermediates.

BACKGROUND OF THE INVENTION

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3K is activated through receptor tyrosine kinase signaling as well as activating mutations in the p110 catalytic subunit of PI3K, loss of the tumor suppressor PTEN, or through rare activating mutations in AKT.

Benzoxazepin compounds have potent and selective activity as inhibitors of the PI3K alpha isoform. Taselisib (GDC-0032, Roche RG7604, CAS Reg. No. 1282512-48-4, Genentech Inc.), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, has potent PI3K activity (Ndubaku, C. O. et al (2013) J. Med. Chem. 56:4597-4610; WO 2011/036280; U.S. Pat. Nos. 8,242,104; 8,343,955) and is being studied in patients with locally advanced or metastatic solid tumors. Taselisib (GDC-0032) is a beta-isoform sparing inhibitor of the PI3K catalytic subunit, 31× more selective for the alpha subunit, compared to beta. Taselisib displays greater selectivity for mutant PI3Kα isoforms than wild-type PI3Kα (Olivero A G et al, AACR 2013. Abstract DDT02-01). Taselisib is currently being developed as a treatment for patients with oestrogen receptor (ER)-positive, HER2-negative metastatic breast cancer (mBC) and non-small cell lung cancer (NSCLC). There is a need for new selective inhibitors of mutant PI3Kα isoforms.

GDC-0077, also known by the IUPAC name: (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide, has potent PI3K activity (WO 2017/001645, US 2017/0015678, Edgar K. et al, #156, "Preclinical characterization of GDC-0077, a specific PI3K alpha inhibitor in early clinical development", and Staben. S. #DDT02-0 "Discovery of GDC-0077, a highly isoform selective inhibitor of PI3K alpha that promotes selective loss of mutant-p110alpha", American Assoc. for Cancer Res. (AACR) annual meeting Apr. 2, 2017, Washington D.C.), and is being studied in patients with locally advanced or metastatic solid tumors. There remains a need for new processes for making benzoxazepin oxazolidinone compounds such as GDC-0077.

SUMMARY OF THE INVENTION

The invention relates to methods of making benzoxazepin oxazolidinone compounds and intermediates thereof.

In one aspect, provided is a process for the preparation of compound 18, having the structure:

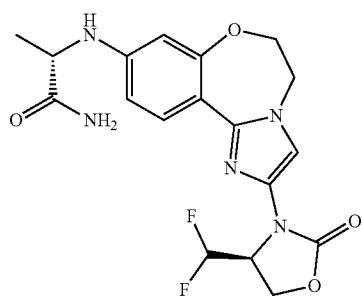

comprising reacting compound 17, having the structure:

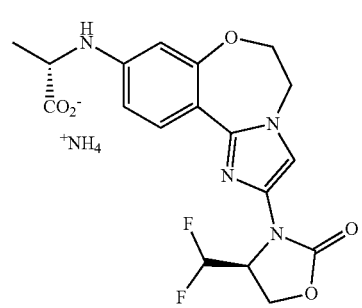

with ammonia (or an ammonia equivalent) and a peptide coupling regent to form compound 18. In some embodiments, the peptide coupling agent is selected from the group consisting of N-(3-dimethylaminopropyl)-N'-ethylcarbodiimide hydrochloride (EDC)/N-hydroxysuccinimide (HOSu), EDC/1-hydroxybenzotriazole (HOBt) and 1,1'-carbonyldiimidazole (CDI). In some embodiments, the peptide coupling reagent is EDC/HOSu.

In some embodiments, compound 17 is prepared by a process comprising reacting compound 16, having the structure:

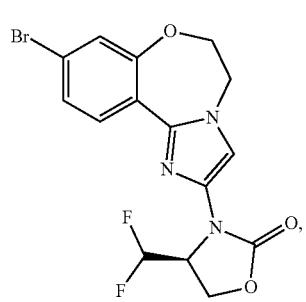

with (S)-2-aminopropanoic acid and a copper (I) catalyst (e.g., copper(I) oxide) to form compound 17.

In some embodiments, compound 16 is prepared by a process comprising reacting compound 15, having the structure:

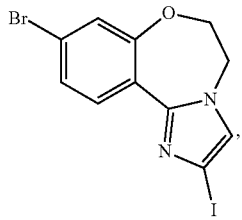

15 with compound 10, having the structure:

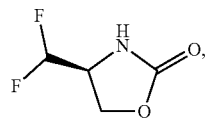

10 a copper salt (e.g., copper(II) acetate) and a ligand (e.g., trans-N,N-dimethylcyclohexane-1,2-diamine or 3,4,7,8-tetramethyl-1,10-phenanthroline) to form compound 16.

In some embodiments, compound 10 is prepared by a process comprising:

(a) reacting compound 6, having the structure:

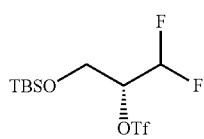

6 with potassium phthalimide to form compound 7, having the structure:

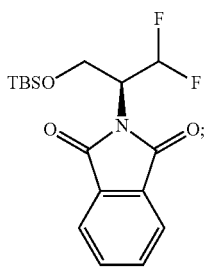

7

(b) reacting compound 7 with hydrazine in water to form compound 8, having the structure:

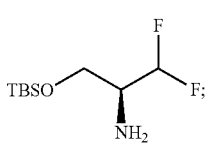

8

(c) reacting compound 8 with hydrochloric acid to form compound 9, having the structure:

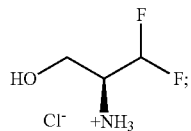

9 and (d) reacting compound 9 with triphosgene to form compound 10.

In some embodiments, compound 15 is prepared by a process comprising:

(a) reacting compound 12, having the structure:

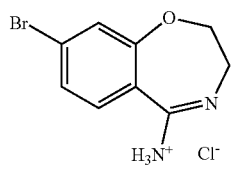

12 with chloroacetaldehyde to form compound 13, having the structure:

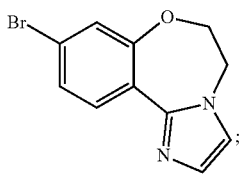

13

(b) reacting compound 13 with N-iodosuccinimide (NIS) to form compound 14, having the structure:

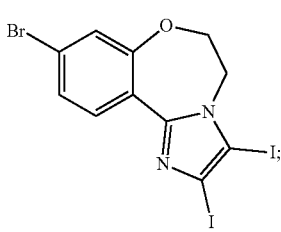

14 and (c) reacting compound 14 with a ethylmagnesium bromide to form compound 15.

In some embodiments, provided is a process for the preparation of compound 18, having the structure:

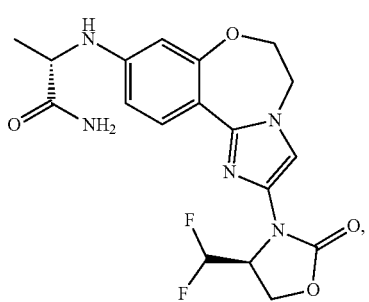

comprising reacting compound 17, having the structure:

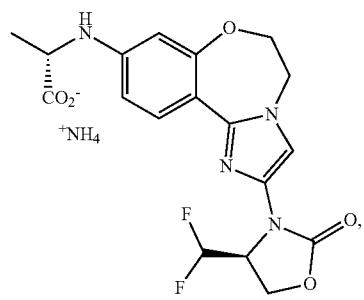

with N-hydroxysuccinimide, ammonia, and N-(3-dimethylaminopropyl)-N'-ethylcarbodiimide hydrochloride to form compound 18.

In some embodiments, compound 17 is prepared by a process comprising reacting compound 16, having the structure:

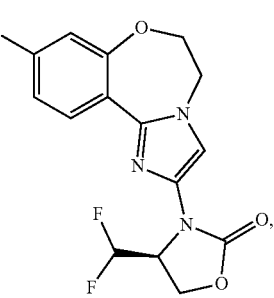

with (S)-2-aminopropanoic acid and copper (I) oxide to form compound 17.

In some embodiments, compound 16 is prepared by a process comprising reacting compound 15, having the structure:

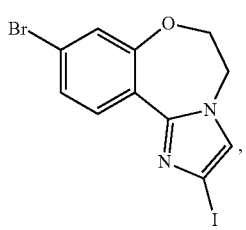

with compound 10, having the structure:

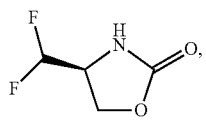

copper (II) acetate and trans-N,N-dimethylcyclohexane-1,2-diamine to form compound 16.

In another aspect, provided is a compound of ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate (compound 17), having the structure:

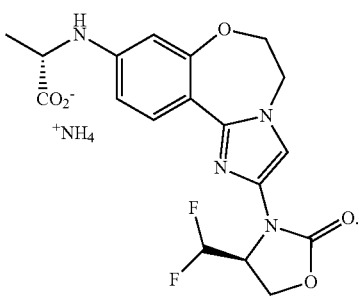

DETAILED DESCRIPTIONS OF THE INVENTION

Definitions

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary* of *Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers (stereocenters), and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

Preparation of Benzoxazepin Oxazolidinone Compounds

The present invention includes processes, methods, reagents, and intermediates for the synthesis of benzoxazepin oxazolidinone compounds, including (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide 18, having the structure:

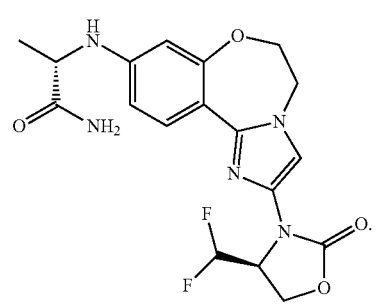

18

It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

In one aspect, provided is a process for the preparation of compound 18, having the structure:

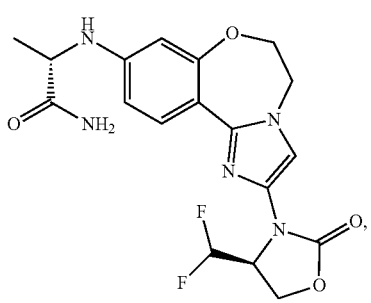

comprising reacting compound 17, having the structure:

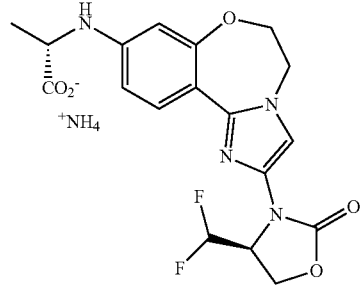

with ammonia or an ammonia equivalent through an amide bond formation reaction (i.e., in the presence of or by contacting with one or more peptide coupling reagents).

The amide bond formation reaction between compound 17 and ammonia or ammonia equivalent to form compound 18 can be facilitated using peptide coupling reagents, for example, a reagent or a combination of two reagents including, but not limited to, N-hydroxysuccinimide (HOSu) and N-(3-dimethylaminopropyl)-N'-ethylcarbodiimide hydrochloride (EDC), 1-hydroxybenzotriazole (HOBt) and EDC, 1-hydroxy-7-azabenzotriazole (HOAt) and EDC, 2-hydroxypyridine-1-oxide and EDC, ethyl (hydroxyimino)cyanoacetate (Oxyma) and EDC, 3-[bis(dimethylamino)methyliumyl]-3H-benzotriazol-1-oxide hexafluorophosphate (HBTU), 1-[bis(dimethylamino)methylene]-1H-1,2,3-triazolo[4,5-b]pyridinium 3-oxide hexafluorophosphate (HATU), and 1,1'-carbonyldiimidazole (CDI). The dehydrating reagent EDC can be replaced with other carbodiimides such as N,N'-diisopropylcarbodiimide (DIC) or N,N-dicyclohexylcarbodiimide (DCC).

In some embodiments, the process for the preparation of compound 18 comprises reacting compound 17 with ammonia or an ammonia equivalent and a peptide coupling regent. In some embodiments, the peptide coupling regent comprises a carbodiimide (e.g., EDC), and an auxiliary reagent (e.g., HOSu or HOBt). In some embodiments, the peptide coupling regent comprises CDI. Coupling reagents such as EDC/HOSu, EDC/HOBt or CDI provide processes with higher efficiency and lower costs, and environmentally benign by-products that are easier to remove, compared to processes using coupling reagents such as HATU and HBTU, especially for syntheses on kilogram and above scales. In some embodiments, the process for the preparation of compound 18 comprises reacting compound 17 with ammonia or an ammonia equivalent and a peptide coupling regent selected from the group consisting of EDC/HOSu, EDC/HOBt and CDI. In one embodiment, the process for the preparation of compound 18 comprises reacting compound 17 with ammonia, HOSu and EDC.

Examples of ammonia equivalents include, but are not limited to, ammonium acetate, ammonium bicarbonate, ammonium carbamate, ammonium carbonate, ammonium chloride, ammonium hydroxide, and ammonium phosphate.

In some embodiments, compound 17 is prepared by a process comprising reacting compound 16, having the structure:

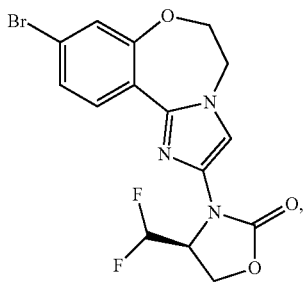

16 with (S)-2-aminopropanoic acid via a copper-catalyzed C—N coupling (i.e., in the presence of or by contacting with a copper catalyst).

In some embodiments, the C—N coupling between compound 16 and (S)-2-aminopropanoic acid to form compound 17 can be performed using a copper catalyst, a base, and a solvent. Examples of the copper catalyst include, but are not limited to, copper (I) oxide, copper (I) chloride, copper (I) bromide, copper (I) iodide, copper (I) trifluoromethanesulfonate, and copper (II) oxide. Examples of the base include, but are not limited to, potassium phosphate, cesium carbonate, and potassium carbonate. The solvent can be chosen from, but not limited to, dimethyl sulfoxide (DMSO), N,N-dimethylformamide (DMF), N,N-dimethylacetamide (DMA), and N-methyl-2-pyrrolidinone (NMP). In some embodiments, compound 17 is prepared by a process comprising reacting compound 16 and a copper (I) catalyst (e.g., copper (I) oxide). In some embodiments, compound 17 is prepared by a process comprising reacting compound 16 and (S)-2-aminopropanoic acid in the presence of a copper (I) catalyst (e.g., copper (I) oxide) and a base (e.g. potassium phosphate tribasic) in a solvent (e.g., DMSO).

The carboxylic acid formed from coupling of compound 16 and (S)-2-aminopropanoic acid is unstable, difficult to isolate, and subject to decomposition. Conversion of the acid to the ammonium salt (compound 17) provides for a stable intermediate compound that can be isolated from the unreacted starting materials and by-products.

In some embodiments, compound 16 is prepared by a process comprising reacting compound 15, having the structure:

15

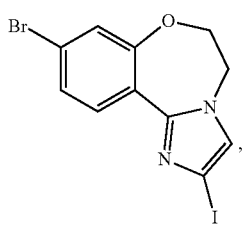

with compound 10, having the structure:

10

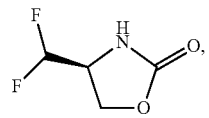

via a copper-catalyzed C—N coupling reaction.

In one embodiment, the C—N coupling reaction between compound 15 and compound 10 to form compound 16 can be performed using a copper salt, a ligand, a base, and a solvent. Examples of suitable copper salts include, but are not limited to, copper (I) oxide, copper (I) chloride, copper (I) bromide, copper (I) iodide, copper (I) trifluoromethanesulfonate, copper (II) acetate, copper (II) chloride, copper (II) bromide, copper (II) iodide, copper (II) oxide, and copper (II) trifluoromethanesulfonate. Examples of suitable ligands include, but are not limited to 1,2-diamines (e.g., as trans-N,N-dimethylcyclohexane-1,2-diamine, trans-1,2-diaminocyclohexane, and N,N'-dimethylethylenediamine), 1,10-phenanthroline or derivatives (e.g., 3,4,7,8-tetramethyl-1,10-phenanthroline), glycine, N,N-dimethylglycine, 2,2,6-trimethylheptane-3,5-dione, and 2-isobutyrylcyclohexan-1-one. Examples of suitable bases include, but are not limited to, potassium phosphate, cesium carbonate, and potassium carbonate. Suitable solvents include, but are not limited to, dimethyl sulfoxide (DMSO), N,N-dimethylformamide (DMF), N,N-dimethylacetamide (DMA), N-methyl-2-pyrrolidinone (NMP), acetonitrile, 2-methyltetrahydrofuran, toluene, and 1,4-dioxane. In some embodiments, compound 16 is prepared by a process comprising reacting compound 15, compound 10, a copper salt (e.g., copper (II) acetate) and a ligand (e.g., trans-N,N-dimethylcyclohexane-1,2-diamine or 3,4,7,8-tetramethyl-1,10-phenanthroline). In some embodiments, compound 16 is prepared by a process comprising reacting compound 15, compound 10, a copper salt (e.g., copper (II) acetate) and a ligand (e.g., trans-N,N-dimethylcyclohexane-1,2-diamine or 3,4,7,8-tetramethyl-1,10-phenanthroline) in the presence of a base (e.g. cesium carbonate or potassium phosphate tribasic) in a solvent (e.g., 2-methyltetrahydrofuran or acetonitrile). In one embodiment, compound 16 is prepared by a process comprising reacting compound 15, compound 10, copper (II) acetate and trans-N,N-dimethylcyclohexane-1,2-diamine in the presence of cesium carbonate in 2-methyltetrahydrofuran. In another embodiment, compound 16 is prepared by a process comprising reacting compound 15, compound 10, copper (II) acetate and 3,4,7,8-tetramethyl-1,10-phenanthroline in the presence of potassium phosphate tribasic in acetonitrile.

In some embodiments, compound 10 is prepared by a process comprising:

(a) reacting compound 6, having the structure:

6

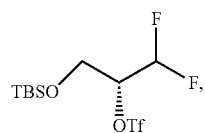

with potassium phthalimide to form compound 7, having the structure:

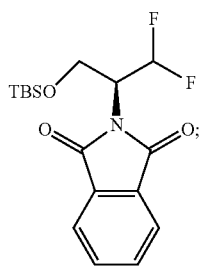

7

(b) reacting compound 7 with hydrazine in water to form compound 8, having the structure:

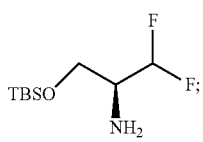

8

(c) reacting compound 8 with hydrochloric acid to form compound 9, having the structure:

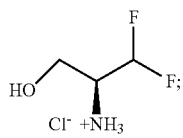

9 and (d) reacting compound 9 with triphosgene to form compound 10.

In some embodiments, compound 15 is prepared by a process comprising:

(a) reacting compound 13, having the structure:

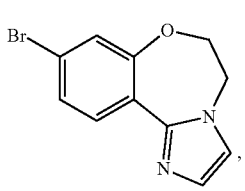

13 with an iodinating reagent (e.g., N-iodosuccinimide (NIS), iodine or iodine monochloride) to form compound 14, having the structure:

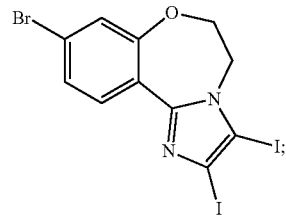

14 and (b) reacting compound 14 with a Grignard reagent (e.g., ethylmagnesium bromide or isopropylmagnesium chloride) to form compound 15.

In some embodiments, compound 13, having the structure:

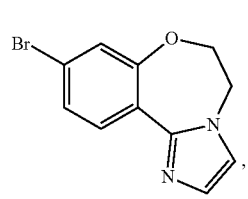

13 is prepared by a process comprising reacting compound 12, having the structure:

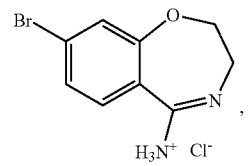

12 with chloroacetaldehyde to form compound 13.

In one embodiment, the condensation reaction between compound 12 and chloroacetaldehyde to form compound 13 can be performed in the presence of a base in a solvent. Suitable bases include, but are not limited to, sodium bicarbonate, potassium bicarbonate, sodium carbonate, and potassium carbonate. Suitable solvents include, but are not limited to, isopropyl alcohol and 2-methyltetrahydrofuran.

Starting materials and reagents for the preparation of compounds in Schemes 1 and 2 are generally available from commercial sources or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes and Examples illustrate the chemical reactions, processes, and methodology for the synthesis of benzoxazepin oxazolidinone compounds, and certain intermediates and reagents.

Scheme 1:

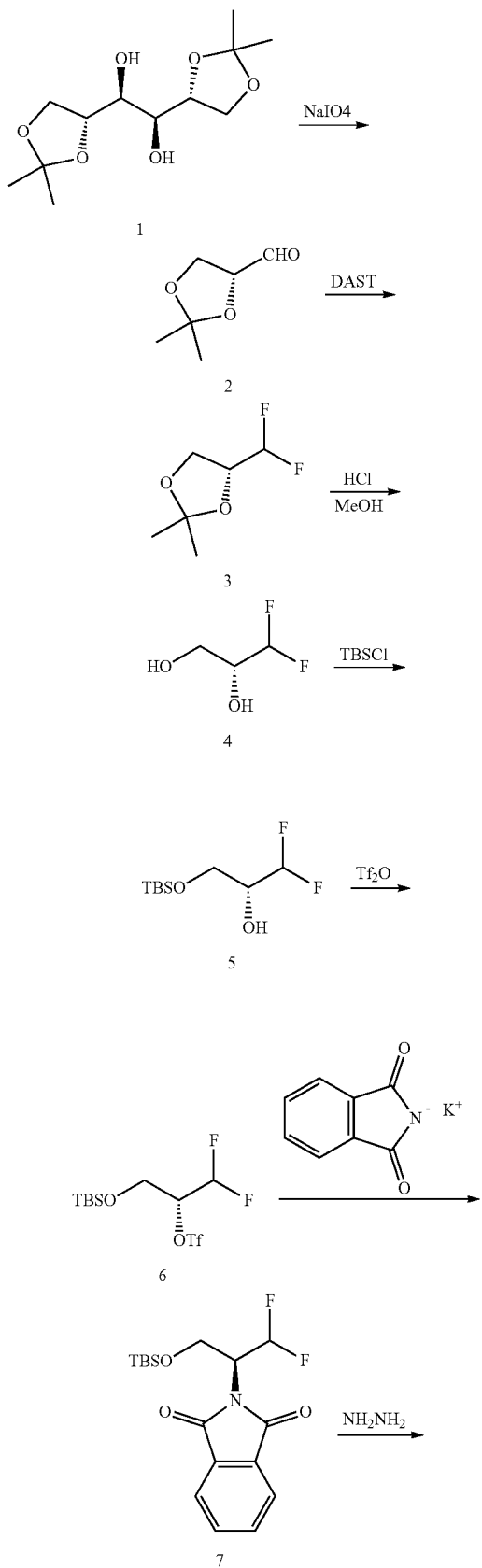

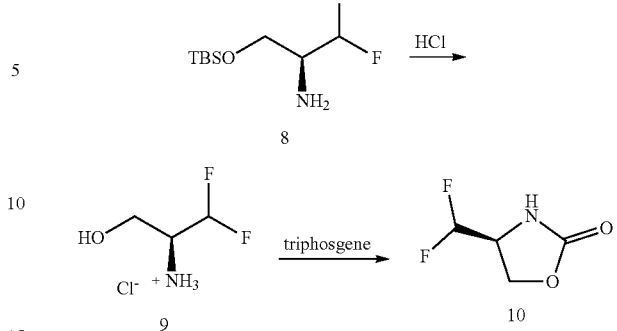

Scheme 1 shows the preparation of (S)-4-(difluoromethyl)oxazolidin-2-one 10. The bis-acetonide of mannitol (D-mannitol, CAS Reg No. 69-65-8), (1S,2S)-1,2-bis((R)-2,2-dimethyl-1,3-dioxolan-4-yl)ethane-1,2-diol 1 was oxidized with sodium periodate to form (R)-2,2-dimethyl-1,3-dioxolane-4-carbaldehyde 2. Deoxofluorination of the aldehyde 2 gave (R)-4-(difluoromethyl)-2,2-dimethyl-1,3-dioxolane 3 using diethylaminosulfur trifluoride (DAST) or other fluorinating reagents such as XtalFluor-E® (CAS Reg No. 63517-29-3) or XtalFluro-M® (CAS Reg No. 63517-33-9). Acetonide cleavage of 3 under acidic conditions gave (R)-3,3-difluoropropane-1,2-diol 4. Chemoselective protection of the primary hydroxyl group of 4 with tert-butyldimethylsilyl chloride gave (R)-3-((tert-butyldimethylsilyl)oxy)-1,1-difluoropropan-2-ol 5. The secondary hydroxyl group of 5 was converted to the triflate with triflic anhydride, trifluoromethanesulfonic anhydride to form (R)-3-((tert-butyldimethylsilyl)oxy)-1,1-difluoropropan-2-yl trifluoromethanesulfonate 6. Displacement of triflate with inversion of stereochemistry by potassium phthalimide gave (S)-2-(3-((tert-butyldimethylsilyl)oxy)-1,1-difluoropropan-2-yl)isoindoline-1,3-dione 7. Cleavage of the phthalimide group of 7 with aqueous hydrazine gave primary amine, (S)-3-((tert-butyldimethylsilyl)oxy)-1,1-difluoropropan-2-amine 8. Silyl group removal of 8 with hydrochloric acid gave (S)-1,1-difluoro-3-hydroxypropan-2-aminium chloride 9 as a hydrochloride salt. Subsequent cyclization of 9 with triphosgene: $CCl_3OCO_2CCl_3$, (bis(trichloromethyl) carbonate (BTC), CAS Reg. No. 32315-10-9 gave (S)-4-(difluoromethyl)oxazolidin-2-one 10.

Scheme 2:

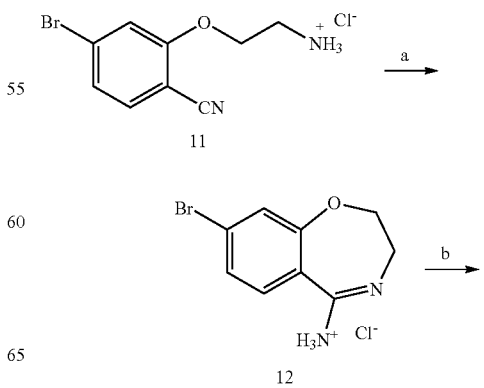

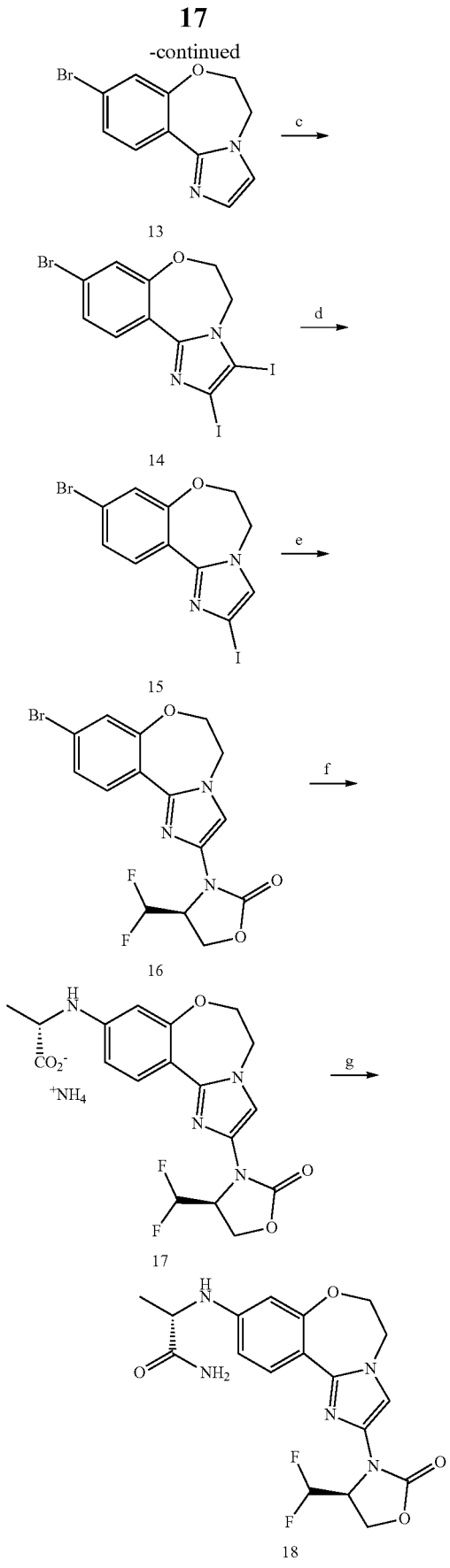

a: i) Mg(OEt)₂, MeOH, MeTHF, ii) HCl, n-PrOH; b: ClCH-CHO, KHCO₃, MeTHF, H₂O, c: NIS, DMF; d: EtMgBr, THF; e: 10, Cu(OAc)₂, trans-N,N'-dimethylcyclohexane-1,2-diamine, Cs₂CO₃, MeTHF; f: i) (S)-2-aminopropanoic acid, Cu₂O, K₃PO₄, DMSO, ii) NH₃, MeOH, THF; g: i) NH₃, HOSu, EDC, THF, ⁱPrOH, ii) EtOH, H₂O.

Scheme 2 shows the preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide 18. 2-(5-Bromo-2-cyanophenoxy)ethan-1-aminium chloride 11 cyclized with magnesium ethoxide, Mg(OEt)₂ in methanol, and acidification with a solution of hydrogen chloride in n-propanol to give of 8-bromo-2,3-dihydrobenzo[f][1,4]oxazepin-5-amine hydrochloride 12. Cyclization of 12 to form the imidazole ring with aqueous chloroacetaldehyde in the presence of potassium bicarbonate as base gave 9-bromo-5,6-dihydrobenzo[f]imidazo[1,2-d][1,4]oxazepine 13. Bis-iodination of the imidazole 13 with N-iodosuccinimide, NIS or other iodinating reagents such as iodine or iodine monochloride gave 9-bromo-2,3-diiodo-5,6-dihydrobenzo[f]imidazo[1,2-d][1,4]oxazepine 14. Selective reduction of 14 via an iodo-metal exchange using a Grignard reagent such as ethylmagnesium bromide or isopropylmagnesium chloride gave 9-bromo-2-iodo-5,6-dihydrobenzo[f]imidazo[1,2-d][1,4]oxazepine 15. Chemoselective replacement of iodide from 15 with (S)-4-(difluoromethyl)oxazolidin-2-one 10 in the presence of a copper catalyst such as copper (II) acetate, a ligand such as trans-N,N'-dimethylcyclohexane-1,2-diamine, 1,10-phenanthroline, or 3,4,7,8-tetramethyl-1,10-phenanthroline, an inorganic base such as cesium carbonate or tripotassium phosphate, and 2-methyltetrahydrofuran or acetonitrile as the solvent gave (S)-3-(9-bromo-5,6-dihydrobenzo[f]imidazo[1,2-d][1,4]oxazepin-2-yl)-4-(difluoromethyl)oxazolidin-2-one 16. Replacement of bromide from 16 with (S)-2-aminopropanoic acid in the presence of a copper catalyst such as copper (I) oxide, an inorganic base such as tripotassium phosphate, and DMSO as the solvent followed by the ammonium salt formation in THF using a solution of ammonia in methanol as the ammonia source gave ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate 17. Conversion of the carboxylate salt 17 to the carboxamide was effected with a solution of ammonia in 2-propanol, an additive such as N-hydroxysuccinimide (HOSu) or 1-hydroxybenzotriazole (HOBt), and a dehydrating reagent such as N-(3-dimethylaminopropyl)-N'-ethylcarbodiimide hydrochloride, EDC in THF to give 18.

EXAMPLES

Scheme 2 Step a: Into a suspension of 2-(5-bromo-2-cyanophenoxy)ethan-1-aminium chloride 11 (20.4 kg, 97.8 wt %, 71.9 mol, 100 mol %) in MeOH (64.0 kg), solid magnesium ethoxide, Mg(OEt)₂ (17.9 kg, 219 mol %) was charged. The mixture was agitated at 25° C. for 30 min and followed by the addition of 2-methyltetrahydrofuran, 2-MeTHF (140 kg), the reaction mixture was heated to reflux and stirred for 40 h. After the reaction was completed, the batch was concentrated to approximately 50 L under reduced pressure below 40° C. Followed by the addition of 2-MeTHF (172 kg), a solution of hydrogen chloride in n-propanol (83.0 kg, 5.00 M) was added below 15° C. The suspension was stirred at 15° C. for 4 h and filtered. The resulting solid was washed with 2-MeTHF (10 kg) and dried under reduced pressure at 50° C. to afford 8-bromo-2,3-dihydrobenzo[f][1,4]oxazepin-5-amine hydrochloride 12 (17.6 kg, 88% yield) as a hygroscopic solid that was used as is for the next step. $^1$H NMR (500 MHz, DMSO-$d_6$) δ 8.32 (s, 3H), 7.74 (d, J=8.3 Hz, 1H), 7.61 (d, J=1.5 Hz, 1H), 7.38 (dd, J=8.3, 1.5 Hz, 1H), 4.44 (t, J=5.2 Hz, 2H), 3.24 (t, J=5.2 Hz, 2H).

Scheme 2 Step b: Into a mixture of 8-bromo-2,3-dihydrobenzo[f][1,4]oxazepin-5-amine hydrochloride 12 (17.6 kg, 63.4 mol, 100 mol %) and 2-MeTHF (122 kg) were charged a 40% chloroacetaldehyde aqueous solution (16.4 kg, 132 mol %) and water (10 kg). The mixture was heated to 40° C. and aqueous potassium bicarbonate solution was charged. The reaction mixture was stirred at 45° C. for 21 h. After the reaction was complete, the reaction mixture was cooled to 20° C., stirred for 30 min, and filtered. The resulting cake was rinsed with 2-MeTHF (33.0 kg) and the combined filtrates were allowed to settle. The resulting organic layer was washed with aqueous sodium bisulfite solution (30 kg), concentrated to approximately 26 L under reduced pressure below 45° C. After the addition of DMF (25 kg), the mixture was concentrated to approximately 26 L under reduced pressure below 45° C. Water (154 kg) was charged at 40° C. followed by the seed of 9-bromo-5,6-dihydrobenzo[f]imidazo[1,2-d][1,4]oxazepine 13 (1.20 kg). The mixture was stirred at 40° C. for another 1.5 h and cooled to 20° C. After stirring for 10 h at 20° C., the suspension was filtered. The resulting solid was washed with water twice (25 kg×2) and dried under reduced pressure at 45° C. to afford 9-bromo-5,6-dihydrobenzo[f]imidazo[1,2-d][1,4]oxazepine 13 (16.3 kg, 97.5 wt %, 95% yield). $^1$H NMR (500 MHz, DMSO-$d_6$) δ 8.33 (d, J=8.6 Hz, 1H), 7.35 (s, 1H), 7.31-7.22 (m, 2H), 7.06 (s, 1H), 4.45 (q, J=5.3 Hz, 4H); FIRMS calcd. For $C_{11}H_{10}BrN_2O$ [M+H]$^+$: 264.9971, found 264.9976.

Scheme 2 Step c: Into a solution of 9-bromo-5,6-dihydrobenzo[f]imidazo[1,2-d][1,4]oxazepine 13 (16.3 kg, 97.5 wt %, 59.9 mol, 100 mol %) in DMF (78.0 kg) was added N-iodosuccinimide, NIS (29.0 kg, 215 mol %) at 40° C. The reaction mixture was slowly heated to 70° C. and stirred for 6 h. After the reaction was complete, 10% aqueous sodium sulfite solution (78.0 kg) was charged at 45° C. followed by water (154 kg). The resulting suspension was stirred at 45° C. for 1 h and cooled to 20° C. After stirring at 20° C. for 8 h, the suspension was filtered. The resulting solid was washed with water (160 kg) and dried under reduced pressure at 45° C. to afford 9-bromo-2,3-diiodo-5,6-dihydrobenzo[f]imidazo[1,2-d][1,4]oxazepine 14 (29.7 kg, 100 wt %, 96% yield) as an off-white solid. $^1$H NMR (500 MHz, DMSO-$d_6$) δ 8.21 (d, J=8.6 Hz, 1H), 7.32-7.24 (m, 2H), 4.51-4.45 (m, 2H), 4.39-4.34 (m, 2H); HRMS calcd. For $C_{11}H_8BrI_2N_2O$ [M+H]$^+$: 516.7904, found 516.7911.

Scheme 2 Step d: Into a solution of 9-bromo-2,3-diiodo-5,6-dihydrobenzo[f]imidazo[1,2-d][1,4]oxazepine 14 (39.4 kg, 76.2 mol, 100 mol %) in tetrahydrofuran, THF (180 kg) was added a solution of 2.0 M ethylmagnesium bromide in 2-methyltetrahydrofuran (44.0 kg, 120 mol %) at 10° C. The reaction mixture was stirred at 10° C. for 2 h. After the reaction was complete, 5% acetic acid (133 kg) was charged while maintaining the batch temperature below 30° C. Ethyl acetate (168 kg) was charged and the resulting mixture was stirred at 20° C. for 1 h. The layers were separated and the aqueous layer was extracted with ethyl acetate (77.8 kg). The combined organic layers were washed with water (76.0 kg) and filtered through a pad of silica gel (19.8 kg). The silica gel pad was rinsed with ethyl acetate (69.6 kg). The combined filtrates were concentrated to approximately 100 L under reduced pressure below 50° C. and THF (146 kg) was added. The resulting mixture was heated to 60° C. until a clear solution was obtained before it was concentrated to approximately 100 L under reduced pressure below 50° C. and then cooled to 30° C. n-Heptane was charged (86.8 kg) and the resulting mixture was stirred at 30° C. for 2 h. The batch was solvent-switched to n-heptane by three cycles of batch concentration under reduced pressure below 35° C. to approximately 180 L and n-heptane addition (47.6 kg×3). The resulting suspension was cooled to 20° C., stirred for 12 h, and filtered. The resulting solid was washed with n-heptane (64.0 kg) and dried under reduced pressure at 45° C. to afford 9-bromo-2-iodo-5,6-dihydrobenzo[f]imidazo[1,2-d][1,4]oxazepine 15 (25.3 kg, 98.7 wt %, 84% yield) as a light tan solid. $^1$H NMR (500 MHz, DMSO-$d_6$) δ 8.23 (d, J=8.6 Hz, 1H), 7.55 (s, 1H), 7.32-7.24 (m, 2H), 4.44 (q, J=5.4 Hz, 4H); HRMS calcd. For $C_{11}H_9BrIN_2O$ [M+H]$^+$: 390.8937, found 390.8949.

Scheme 2 Step e: 9-bromo-2-iodo-5,6-dihydrobenzo[f]imidazo[1,2-d][1,4]oxazepine 15 (6.90 kg, 98.7 wt %, 17.4 mol, 100 mol %) was charged to a reactor, followed by (S)-4-(difluoromethyl)oxazolidin-2-one 10 (2.68 kg, 112 mol %), copper (II) acetate (0.653 kg, 20.6 mol %), and $Cs_2CO_3$ (11.7 kg, 206 mol %). The reactor was evacuated and backfilled with nitrogen three times. 2-Methyltetrahydrofuran (36.0 kg) and trans-N,N-dimethylcyclohexane-1,2-diamine (0.764 kg, 30 mol %) was then charged into the reactor. The reactor was evacuated and backfilled with nitrogen three times. The reaction mixture was heated to 78° C. and stirred for 22 h. After the reaction was complete, a 20 wt % $NaHSO_4$ aqueous solution (42.0 kg) was slowly added while maintaining the internal temperature between 60-70° C. The layers were separated at 65° C. and the aqueous layer was removed. The batch was solvent-switched to acetonitrile via a constant volume distillation under reduced pressure at 60-70° C. by adding acetonitrile (62.3 kg). Water (14.1 kg) was added into the reactor while maintaining the batch temperature between 60-70° C. The suspension was cooled to 20° C. at a rate of 0.5° C./min, stirred for 18 h, and filtered. The resulting solid was washed with a mixture of acetonitrile and water (50 kg, 44:56, w/w) and dried under reduced pressure at 90° C. to afford (S)-3-(9-bromo-5,6-dihydrobenzo[f]imidazo[1,2-d][1,4]oxazepin-2-yl)-4-(difluoromethyl)oxazolidin-2-one 16 as a tan solid (5.85 kg, 91.9 wt %, 77% yield). $^1$H NMR (500 MHz, $CDCl_3$) δ 8.22 (d, J=8.8 Hz, 1H), 7.31 (s, 1H), 7.28-7.19 (m, 2H), 6.71-6.62 (m, 1H), 4.90 (ddd, J=24.0, 9.3, 3.8 Hz, 1H), 4.75 (dd, J=9.4, 3.9 Hz, 1H), 4.56 (t, J=9.3 Hz, 1H), 4.51-4.44 (m, 2H), 4.41-4.35 (m, 2H); FIRMS calcd. For $C_{15}H_{13}BrF_2N_3O_3$ [M+H]$^+$: 400.0103, found 400.0134.

Scheme 2 Step f: (S)-3-(9-bromo-5,6-dihydrobenzo[f]imidazo[1,2-d][1,4]oxazepin-2-yl)-4-(difluoromethyl)oxazolidin-2-one 16 (3.96 kg, 91.9 wt %, 9.19 mol, 100 mol %) was charged to a reactor, followed by (S)-2-aminopropanoic acid (L-alanine) (2.49 kg, 307 mol %), $K_3PO_4$ (5.84 kg, 303 mol %), and DMSO (19.9 kg). The mixture was sparged with nitrogen for 1 h and heated to 95° C. A slurry of copper (I) oxide (67.1 g, 5.16 mol %) in DMSO (2.21 kg) that was pre-sparged with nitrogen for 30 min was then transferred to the reactor. The reaction mixture was stirred at 95° C. for 4 h. After the reaction was complete, the reaction mixture was cooled to 20° C. DCM (37.3 kg) was added to the reactor, followed by water (24.2 kg). The layers were separated and the organic layer was removed. The aqueous layer was washed with dichloromethane, DCM (26.6 kg) one more time. THF (35.2 kg) and an aqueous sodium bisulfate solution (19 wt %, 20.7 kg) were charged to the reactor sequentially. The layers were separated and the aqueous layer was removed. The organic layer was washed with 15 wt % brine (2×12 kg). SiliaMetS® DMT (Silicycle Inc., 1.60 kg) was charged and the batch was stirred at 25° C. for 15 h and filtered to scavenge residual metal. SiliaMetS® DMT is the silica-bound equivalent of 2,4,6-trimercaptotriazine (trithiocyanuric acid, TMT), and a versatile metal scavenger for a variety of metals including ruthenium catalysts and hindered Pd complexes. Tetrahydrofuran, THF (24.8 kg) was used to rinse the filter. The combined filtrates were heated to 50° C. A 7 N solution of ammonia in methanol (1.02 kg, 100 mol %) was added followed by a slurry of seeds (ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate 17, 19.5 g) in THF (0.395 kg). The resulting suspension was stirred at 50° C. for 2 h and a constant volume distillation was conducted at 40-60° C. under reduced pressure to remove residual water by adding anhydrous THF (60.1 kg). A 7 N solution of ammonia in methanol (1.02 kg, 100 mol %) was added. The suspension was stirred at 50° C. for 15 h and filtered. The resulting solid was washed with THF (21.8 kg) and dried under reduced pressure at 25° C. to afford ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate 17 as a beige solid (3.19 kg, 98.0 wt %, 81% yield). $^1$H NMR (DMSO-$d_6$) δ 7.97 (d, J=8.8 Hz, 1H), 7.16 (s, 1H), 6.74-6.69 (m, 1H), 6.38 (dd, J=9.0, 2.2 Hz, 1H), 6.07 (d, J=2.2 Hz, 1H), 5.02-4.91 (m, 1H), 4.64-4.52 (m, 2H), 4.40-4.30 (m, 4H), 3.63 (q, J=6.1, 5.5 Hz, 1H), 1.27 (d, J=6.7 Hz, 3H). HRMS calcd. For $C_{18}H_{19}F_2N_4O_5$ [M+H]$^+$: 409.1318, found 409.1318.

Scheme 2 Step g: Ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate 17 (5.60 kg, 13.2 mol, 100 mol %) was charged to a reactor, followed by N-hydroxysuccinimide, HOSu (1.52 kg, 102 mol %) and THF (49.6 kg). The batch was sparged with nitrogen for 40 min and cooled to 10° C. A 2 N solution of ammonia in 2-propanol (5.05 kg, 101 mol %) and N-(3-dimethylaminopropyl)-N'-ethylcarbodiimide hydrochloride, EDC (5.20 kg, 210 mol %) were charged sequentially to the reactor. The reaction mixture was stirred at 10° C. for 20 h. After the reaction was complete, the mixture was warmed up to 20° C. and 15 wt % brine (33.7 kg) was added. The layers were separated at 35° C. and the aqueous layer was removed. The organic layer was washed sequentially with 15 wt % brine (2×16.9 kg) and a mixture of 15 wt % brine (8.97 kg) and 28.0-30.0 wt % ammonium hydroxide (7.55 kg) and then filtered through a polishing filter unit. The filter unit was rinsed with THF (5.05 kg). The combined filtrates were distilled under reduced pressure at 50° C. to approximately half of its original volume. Ethanol (8.90 kg) was charged at 50° C., followed by a slurry of seeds ((S)-2-((2-((S)-4-(difluoromethyl)-2-oxooxazolidin-3-yl)-5,6-dihydrobenzo[f]imidazo[1,2-d][1,4]oxazepin-9-yl)amino)propanamide 18, 27.1 g) in ethanol (0.340 kg). The resulting suspension was stirred at 50° C. for 30 min and solvent-switched to ethanol via a constant volume distillation under reduced pressure at 40-60° C. by adding ethanol (39.9 kg). Water (0.379 kg) was added at 50° C. The suspension was cooled to 20° C., stirred for 23 h, and filtered. The resulting solid was washed with a 90:10 (w/w) mixture of ethanol and water (27.9 kg) and dried under reduced pressure at 80° C. to afford (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide 18 as a light pink solid (4.37 kg, 99.7 wt %, 83% yield). $^1$H NMR (600 MHz, CD$_3$CN) δ 8.08 (d, J=8.8 Hz, 1H), 7.11 (s, 1H), 6.86-6.50 (m, 1H), 6.41 (dd, J=8.8, 2.3 Hz, 1H), 6.12 (d, J=2.4 Hz, 1H), 4.87 (dd, J=23.8, 8.8 Hz, 1H), 4.67-4.50 (m, 2H), 4.43-4.33 (m, 2H), 4.33-4.26 (m, 2H), 3.82 (q, J=7.0 Hz, 1H), 1.41 (d, J=7.0 Hz, 3H) (Note: N—H protons were omitted for clarity); $^{13}$C NMR (151 MHz, CD$_3$CN) δ 178.2, 157.0, 155.1, 149.1, 141.6, 135.4, 130.8, 113.3, 108.9, 108.1, 107.7, 102.1, 68.5, 61.7, 56.1, 53.1, 49.6, 18.2; HRMS calcd. For $C_{18}H_{20}F_2N_5O_4$ [M+H]$^+$: 408.1478, found 408.1473.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A process for the preparation of compound 18, having the structure:

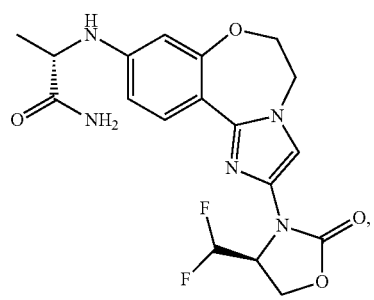

comprising reacting compound 17, having the structure:

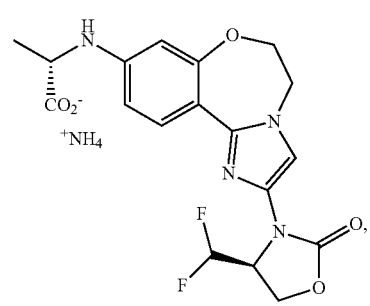

with ammonia or an ammonia equivalent and a peptide coupling reagent selected from the group consisting of N-(3-dimethylaminopropyl)-N'-ethylcarbodiimide hydrochloride/N-hydroxysuccinimide; N-(3-dimethylaminopropyl)-N'-ethylcarbodiimide hydrochloride/1-hydroxybenzotriazole; and 1,1'-carbonyldiimidazole (CDI), to form compound 18.

2. The process of claim 1, wherein the peptide coupling reagent is N-(3-dimethylaminopropyl)-N'-ethylcarbodiimide hydrochloride/N-hydroxysuccinimide.

3. The process of claim 1 wherein compound 17 is prepared by a process comprising reacting compound 16, having the structure:

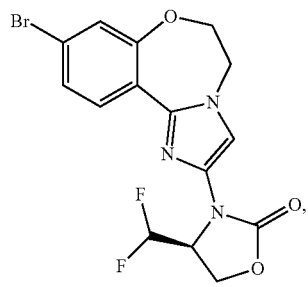

16 with (S)-2-aminopropanoic acid and a copper(I) catalyst to form compound 17.

4. The process of claim 3, wherein the copper(I) catalyst is copper(I) oxide.

5. The process of claim 3 wherein compound 16 is prepared by a process comprising reacting compound 15, having the structure:

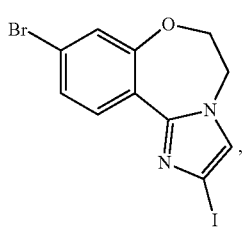

15 with compound 10, having the structure:

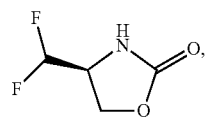

10 a copper salt and a ligand to form compound 16.

6. The process of claim 5, wherein the copper salt is copper(II) acetate.

7. The process of claim 5, wherein the ligand is trans-N,N-dimethylcyclohexane-1,2-diamine.

8. The process of claim 5, wherein the ligand is 3,4,7,8-tetramethyl-1,10-phenanthroline.

9. The process of claim 5, wherein compound 10 is prepared by a process comprising:

(a) reacting compound 6, having the structure:

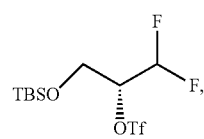

6 with potassium phthalimide to form compound 7, having the structure:

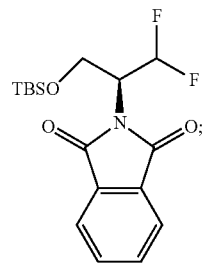

7

(b) reacting compound 7 with hydrazine in water to form compound 8, having the structure:

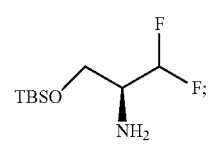

8

(c) reacting compound 8 with hydrochloric acid to form compound 9, having the structure:

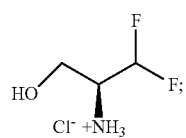

9 and (d) reacting compound 9 with triphosgene to form compound 10.

10. The process of claim 5, wherein compound 15 is prepared by a process comprising:

(a) reacting compound 12, having the structure:

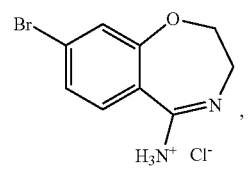

12 with chloroacetaldehyde to form compound 13, having the structure:

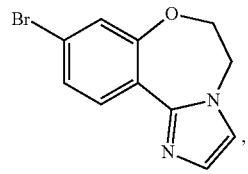

13

(b) reacting compound 13 with N-iodosuccinimide to form compound 14, having the structure:

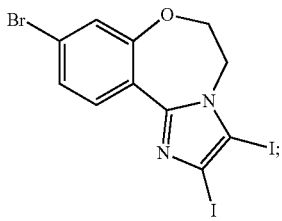

14 and (c) reacting compound 14 with a ethylmagnesium bromide to form compound 15.

11. Ammonium (S)-2-((2-((S)-4-(difluoromethyl)-2-oxooxazolidin-3-yl)-5,6-dihydrobenzo[f]imidazo[1,2-d][1,4]oxazepin-9-yl)amino)propionate (compound 17), having the structure:

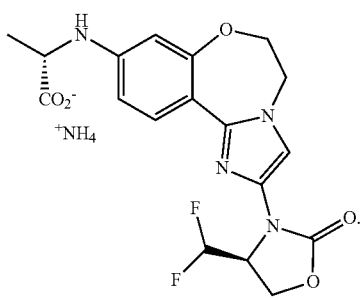

17

12. A process for the preparation of compound 18, having the structure:

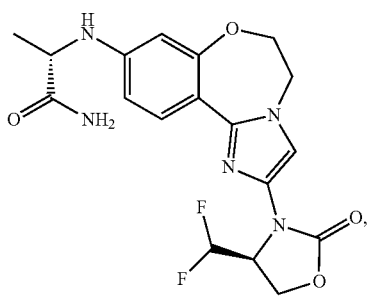

18 comprising reacting compound 17, having the structure:

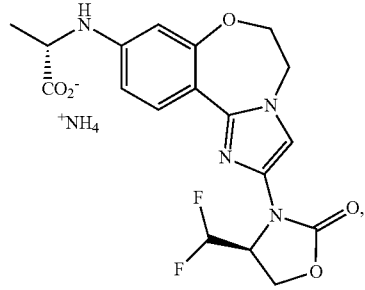

17 with ammonia and a peptide coupling reagent which is N-(3-dimethylaminopropyl)-N'-ethylcarbodiimide hydrochloride/N-hydroxysuccinimide, to form compound 18.

13. The process of claim 12, wherein compound 17 is prepared by a process comprising reacting compound 16, having the structure:

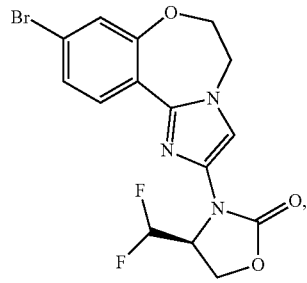

16 with (S)-2-aminopropanoic acid and a copper(I) catalyst to form compound 17.

14. The process of claim 13, wherein the copper(I) catalyst is copper(I) oxide.

15. The process of claim 13 wherein compound 16 is prepared by a process comprising reacting compound 15, having the structure:

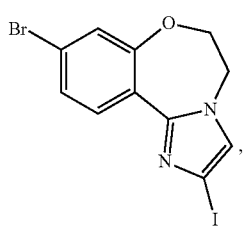

15 with compound 10, having the structure:

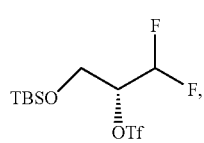

10 a copper salt and a ligand to form compound 16.

16. The process of claim 15, wherein the copper salt is copper(II) acetate.

17. The process of claim 16, wherein the ligand is trans-N,N-dimethylcyclohexane-1,2-diamine.

18. The process of claim 15, wherein the ligand is 3,4,7,8-tetramethyl-1,10-phenanthroline.

19. The process of claim 15, wherein compound 10 is prepared by a process comprising:

(a) reacting compound 6, having the structure:

6 with potassium phthalimide to form compound 7, having the structure:

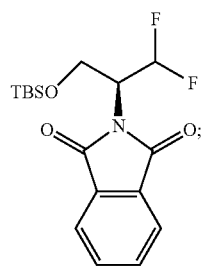

7

(b) reacting compound 7 with hydrazine in water to form compound 8, having the structure:

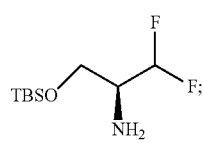

8

(c) reacting compound 8 with hydrochloric acid to form compound 9, having the structure:

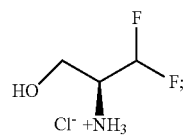

9 and (d) reacting compound 9 with triphosgene to form compound 10.

20. The process of claim 15, wherein compound 15 is prepared by a process comprising:

(a) reacting compound 12, having the structure:

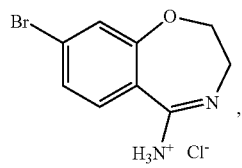

12 with chloroacetaldehyde to form compound 13, having the structure:

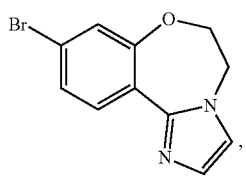

13

(b) reacting compound 13 with N-iodosuccinimide to form compound 14, having the structure:

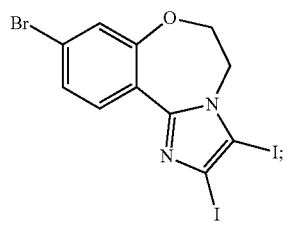

14 and (c) reacting compound 14 with a ethylmagnesium bromide to form compound 15.

* * * * *